(12) United States Patent
Stevens

(10) Patent No.: US 6,583,415 B2
(45) Date of Patent: Jun. 24, 2003

(54) METHOD AND SYSTEM FOR DYNAMICALLY POLARIZING ELECTRO-OPTIC SIGNALS

(75) Inventor: Rick C. Stevens, Apple Valley, MN (US)

(73) Assignee: Lockheed Martin Corporation, Bethesda, MD (US)

( * ) Notice: Subject to any disclaimer, the term of this patent is extended or adjusted under 35 U.S.C. 154(b) by 25 days.

(21) Appl. No.: 09/845,793

(22) Filed: Apr. 30, 2001

(65) Prior Publication Data

US 2002/0158203 A1 Oct. 31, 2002

(51) Int. Cl.[7] .................................................. G01J 4/02
(52) U.S. Cl. .................... 250/330; 250/341.3; 250/225; 356/364
(58) Field of Search ............................... 250/330, 332, 250/338.1, 338.3, 338.4, 349, 350, 351, 341.3, 559.09, 225; 356/5.14, 364, 366

(56) References Cited

U.S. PATENT DOCUMENTS

| | | | | |
|---|---|---|---|---|
| 5,182,624 A | * | 1/1993 | Tran et al. .................... 257/40 |
| 5,543,608 A | * | 8/1996 | Rantalainen ................. 235/454 |
| 5,661,560 A | * | 8/1997 | Ozaki .......................... 356/364 |
| 5,828,500 A | * | 10/1998 | Kida et al. ................... 359/798 |
| 6,211,957 B1 | * | 4/2001 | Erdogan et al. ............ 356/364 |

* cited by examiner

*Primary Examiner*—Constantine Hannaher
*Assistant Examiner*—Timothy J Moran
(74) *Attorney, Agent, or Firm*—Patrick M. Hogan; Glenn W. Bowen

(57) ABSTRACT

A sensor arrangement and system facilitate the measurement of polarized light intensities for use in object identification and classification. In an example embodiment, an imaging sensor for polarizing light from a light source includes an array of light detecting elements that converts light into a plurality of photocurrent signals. The sensor also includes a rotatable disk positioned between a light source and the light detecting array and parallel to the light detecting array. The rotatable disk includes a plurality of linear members that are opaque and parallel to each other that polarize light from the light source passed to the light-detecting array. The sensor further includes a circuit arrangement configured to generate a data set of polarization vector components, the polarization vector components being generated as a function of a set of the photocurrent signals that are sampled as a function of a position of the rotating disk.

16 Claims, 2 Drawing Sheets

METHOD AND SYSTEM FOR DYNAMICALLY POLARIZING ELECTRO-OPTIC SIGNALS

FIELD OF THE INVENTION

The present invention generally relates to imaging systems for the detection and recognition of remote objects. More particularly, the invention relates to improving polarization data acquisition using polarimetric sensors.

BACKGROUND

Infrared radiation is often used to detect objects where visible light is either blocked or not present. Thus, it is possible to use infrared detection at night or through clouds, dust or haze. An infrared detector can be in the form of either a single detecting element or an array of such elements to produce an image. The optical receiver can be a photoelectric detector such as an amorphous silicon photodetector or a photodiode that converts the optical signal into an electrical signal that is conducted to an input pin on a receiving IC. A portion of the light reflected off of the surface of an object is detected by a photodetector array.

A limitation when using thermal intensity for search and identification is that thermal intensity gives only one parameter whereas the surface orientation on a three-dimensional object is specified by two angles. Information about the two angles of surface orientation is often contained in the polarization of the thermal radiation (i.e., infrared). Polarization of the thermal radiation also gives useful information about the surface properties of the object. Man-made objects have unnaturally smooth surfaces, which results in radiation with greater polarization. Natural backgrounds such as grass, trees, dirt, and sand generate radiation that is less polarized.

The polarization properties of a beam of incoherent radiation emitted or reflected from a object's surface can be completely described at a given wavelength by the four Stokes parameters, (I, Q, U and V). The first Stokes parameter I is a measure of the total intensity of radiation. The second parameter Q measures the amount of linear polarization in the horizontal direction. The third parameter U measures the amount of linear polarization at 45 degrees from the horizontal. The fourth parameter V is associated with the circular polarization. Photodetector sensors are used today to capture polarization data. However to improve the accuracy of the object detected additional polarization data is needed. Developing a custom sensor array with additional detector elements is one approach to obtaining more data; however this approach has resulted in an increase in expense and complexity of the sensor array used to capture the polarization data.

Wire grid polarizers have been used in the past to gather polarization data. Wire grid polarizers utilize parallel lines of conductive materials of 5$\mu$ (micron) scale width spacing deposited onto an infrared transparent substrate. The light having polarization parallel to the conducting lines is absorbed and/or reflected, while the light having polarization perpendicular to the lines is transmitted. Wire grid polarizers have some advantage for operation in the 3.5 $\mu$m to 14.5 $\mu$m wavelength range since they are more compact and there is no beam offset or angular displacement at normal incidence. However, wire grid polarizers are expensive, extremely delicate and are easily damaged in handling.

Another challenge involves developing thermal sensing systems that utilize commercial off the shelf (COTS) parts versus custom designed parts since many manufacturers prefer to manufacture high volume parts and charge a premium to provide the low volume, custom parts. The use of COTS parts in these systems would not only reduce cost and manufacturing cycle time but would also simplify field repair of such thermal sensing systems.

A system and an arrangement that addresses the aforementioned problems, as well as other related problems, are therefore desirable.

SUMMARY OF THE INVENTION

The present invention is directed to addressing the above and other needs in connection with electro-optic sensors used in target acquisition systems. The present approach facilitates the extraction of polarization data to be used in polarization algorithms for identifying and classifying targets.

According to one aspect of the invention, an imaging sensor for polarizing light includes an array of light detecting elements that converts light into a plurality of photocurrent signals. The sensor also includes a rotatable disk positioned in between a light source and the light detecting array and parallel to the light detecting array. The rotatable disk includes a plurality of linear members that are opaque and parallel to each other that polarize light from the light source passed to the light-detecting array. The sensor further includes a circuit arrangement configured to generate a data set of polarization vector components, the polarization vector components being generated as a function of a set of the photocurrent signals that are sampled as a function of a position of the rotating disk.

According another aspect of the invention, a polarimetric infrared imaging sensor arrangement simplifies generating polarization vector data from light reflected from an object, wherein the vector data is used for object identification. The sensor arrangement includes a photodetector array having an optically transparent surface that is arranged to convert any detected light reflected from the object into a plurality of photocurrent signals. The sensor arrangement also includes a rotatable disk positioned between the object and the photodetector array and parallel to the photodetector array, the rotatable disk including a plurality of linear members that are opaque and parallel to each other, whereby the reflected light is polarized and passed to the photodetector array. A rotator arrangement is engaged with a portion of the rotatable disk and arranged to impart a selected rotation rate to the rotatable disk. A circuit arrangement is coupled to the photodetector array and is configured to generate a set of polarization vector data by sampling the photocurrent signals.

According to yet another aspect of the invention, a method facilitates identifying an object in a target classification system by using light reflected from the object as data. In particular, the method includes converting light detected from the object into a plurality of photocurrent signals using a photodetector array. A disk, positioned in between a light source and the photodetector array and parallel to the array, is then rotated to polarize light from the light source before being detected by the photodetector array. The rotatable disk includes a plurality of linear members that are opaque and are parallel to each other. The plurality of photocurrent signals are then sampled at the photodetector array at selected disk angles as the disk rotates. A data set of polarization vector components is then generated from the sampled plurality of photocurrent signals.

It will be appreciated that various other embodiments are set forth in the Detailed Description and Claims that follow.

BRIEF DESCRIPTION OF THE DRAWINGS

Various aspects and advantages of the invention will become apparent upon review of the following detailed description and upon reference to the drawings in which.

DETAILED DESCRIPTION

The present invention is generally directed to an arrangement and system for generating a set of Stokes vector components for use in remote target classification and recognition. The system of the present invention greatly simplifies the gathering and the sampling of polarization data while reducing the complexity of current imaging systems. Micro electro-mechanical systems (MEMS) technology, as well as LIGA technology, is also utilized in the design and manufacture of the compact polarimetric electro-optic imaging sensor of the present invention. While the present invention is not necessarily limited to such an application, the invention will be better appreciated using a discussion of example embodiments in such a specific context.

In an example embodiment, a plurality of polarimetric imaging sensors are formed in an image sensor array that is incorporated into a target acquisition system. The polarizing element positioned between the sensor array and the light source (or reflected light) to be detected consists of a polarizing lens made from a linear grid of metal wires on a dielectric substrate that is either fixed to a rotatable disk or is itself a rotating disk. In this way, any linear polarization state can be obtained simply by rotating the disk into a desired angular position and measurements taken.

Objects are identified and classified using three frames of reference that include infrared intensity (I), percent of polarization (P) and angle of the polarization (Ö). Normally, the infrared intensity is known and P and Ö are determined using the following formulae:

$$Ö = \tfrac{1}{2} \operatorname{Arctan}[U/Q]$$

$$P = [Q^2 + U^2]/I$$

Where I, Q and U are Stokes parameters that are used to represent the polarization characteristics of an electromagnetic wave. For a totally polarized light, the Stokes parameters have the following relationship:

$$I^2 = Q^2 + U^2 + V^2$$

The values of I, Q and U are obtained by passing light waves through linear polarizers at various angles, including 0°, 45°, 90° and 135°. Once the polarized light intensities i at various angles are obtained the Stokes parameters are determined using the following formulae:

$$I = \tfrac{1}{2}(i_0 + i_{45} + i_{90} + i_{135})$$

$$Q = i_0 - i_{90}$$

$$U = i_{45} - i_{135}$$

The difficulty in determining three reference frames has been in the process of obtaining the polarized light intensity values (i) at multiple angles. Elaborate light sensor arrays have been developed that detect light intensities at various angles but they have been too mechanically complex to manufacture and maintain. The present approach provides a simple way of obtaining the desired number of light intensity values to arrive at the three reference frames. Where precision is important additional light intensity data is easily obtainable with the image sensor and sensor system of the present invention.

Figure 1A:
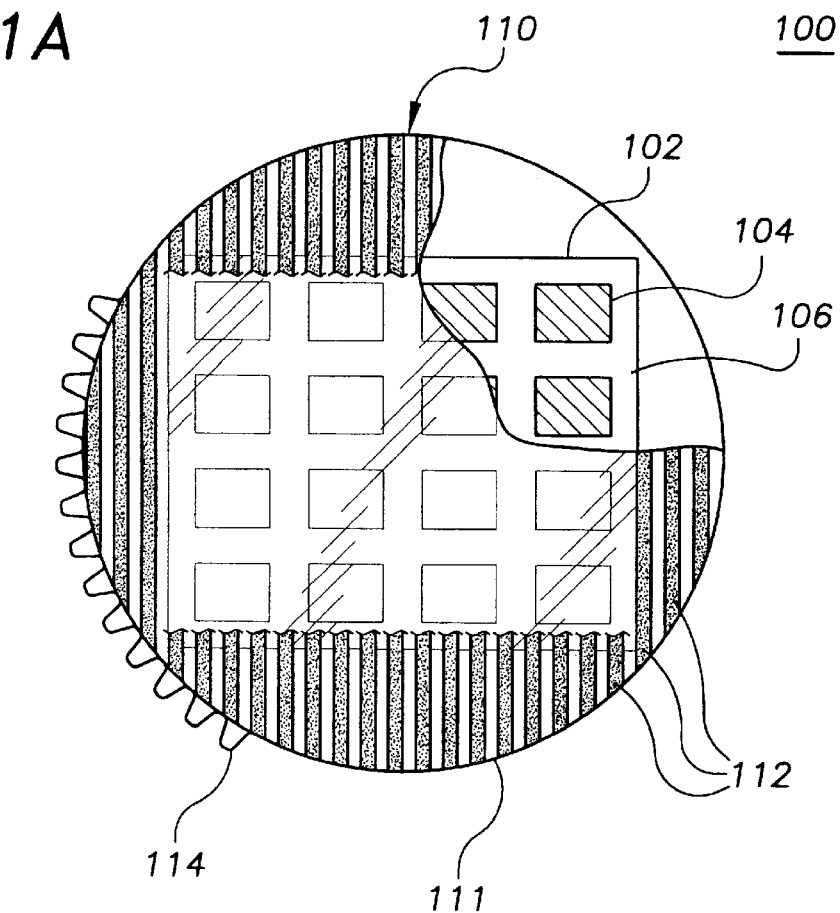
FIGS. 1A and 1B are the top and side views of an example imaging sensor made in accordance with one embodiment of the present invention.
Figure 1B:
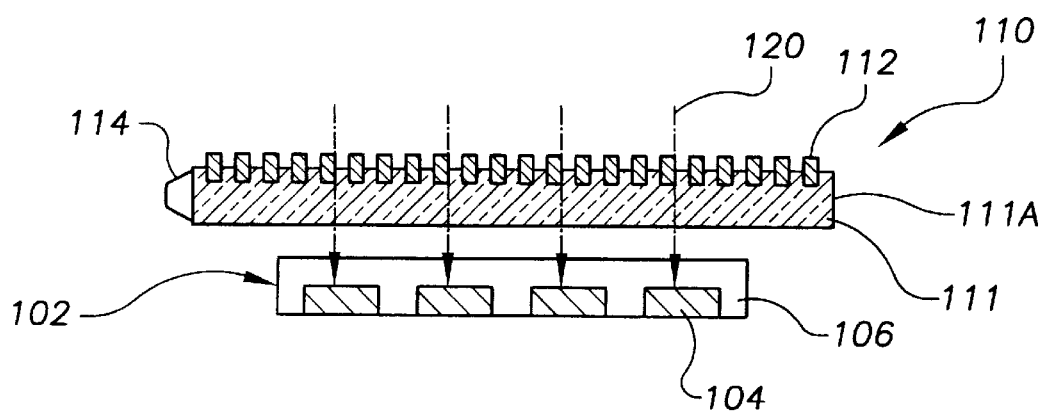

Referring now to the figures, FIGS. 1A and 1B are top and side views of an example embodiment of an imaging sensor 100 made in accordance with the teachings of the present invention. Imaging sensor 100 is utilized in a target acquisition system for polarizing light reflected off of an object being identified and classified. Sensor 100 includes a photodetector array 102, which is an array of light detecting elements, that converts light into a plurality of photocurrent signals. Photodetector arrays are comprised of a number of individual photodetectors 104 mounted within a translucent material 106 and integrated upon an IC chip. The integration of photodetectors on monocrystalline silicon is well known in the optics industry. Each photodetector generates photocurrent signals that communicate with current measurement circuitry (not shown). Individual photodetectors and current measurement circuits are normally integrated on a single integrated circuit (IC) chip.

Sensor 100 includes a rotatable disk 110 positioned in between a light source (or the light reflected back from the object to be identified) and photodetector array 102, with the disk being parallel to array 102. Rotatable disk 110 includes a plurality of linear members 112, which are opaque and are parallel to each other, that polarize light 120 from the light source before being detected by array 102. A grating, an example portion of which is referenced by lines 112 and which operates similar to a directional filter, filters out all light waves that arc nut in the same polarization pattern. Optical energy impinging on disk 110 is divided into various polarization angles based on the angular position of disk 110. This will be discussed in further detail in connection with FIGS. 3A–3D. In this example embodiment, disk 110 is made from an optically translucent material that has a fused silica grating thereon to polarize light 120 passing through the disk. In another example embodiment, disk 110 is made from a series of wire members, which are parallel to each other, tat also polarize light 120 before being detected by array 102.

Disk 110 is rotated in front of array 102 via a set of gear teeth 114 disposed on a circumference edge 111 of die disk. In another embodiment, a bare surface 111A of edge 111 is engaged with a roller mechanism to effect the rotation of disk 110. Disk 110 is spaced sufficiently from array 102 to facilitate the rotation of the disk but to avoid optical attenuation through disk 110 from having the disk too far away from array 102. Light passing through disk 110 is lost through scattering when the spacing between array 102 and disk 110 is too large.

Due to the small size of disk 110, MEMS and LIGA technologies are used fabricate the disk. Microelectromechanical structures (MEMS) are fabricated in polysilicon using thin layers of polysilicon alternating with thin layers of silicon dioxide ($SiO_2$). Upon completion of the fabrication process all the $SiO_2$ layers are dissolved away using an etching solution. The resulting polysilicon parts are free to move. The depth, width and spacing of opaque lines 112 are a function of the wavelength of the light being detected by array 102. Since the wavelength of operation is anticipated to fall between 3 and 5 µm, the polysilicon disk 110 appears as a transparent dielectric having a refractive index of about 3.5. The polysilicon layers are about 2–3 µm thick, with disk 110 having a diameter of about 2 mm. The use of either MEMS or LIGA technology in making polarizing disk 110 depends on the size of polarizing disk needed in the application. For diameters smaller than 2 mm, a MEMS approach is preferred, whereas larger diameters suggest a LIGA solution.

Figure 2:
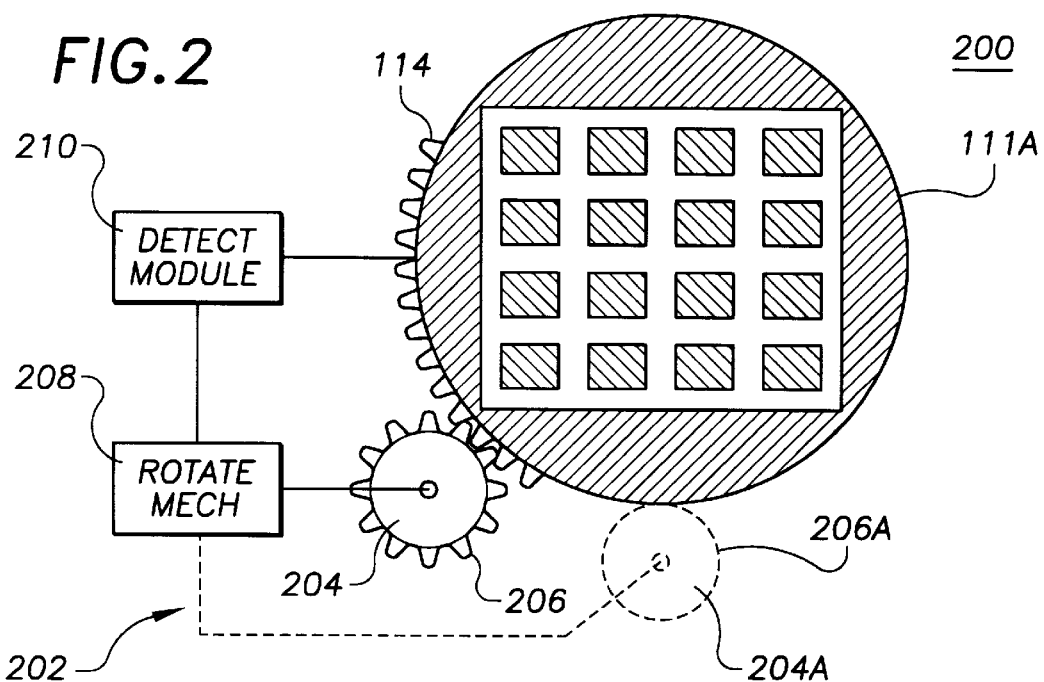
FIG. 2 is a rear view of an example imaging system made in accordance with one embodiment of the invention.
Figure 3A:
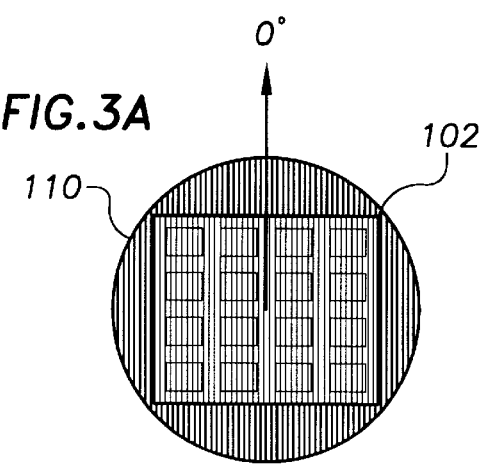
FIGS. 3A–3D show examples of the various angles of the rotatable disk of the imaging system in accordance with an embodiment of the invention.
Figure 3B:
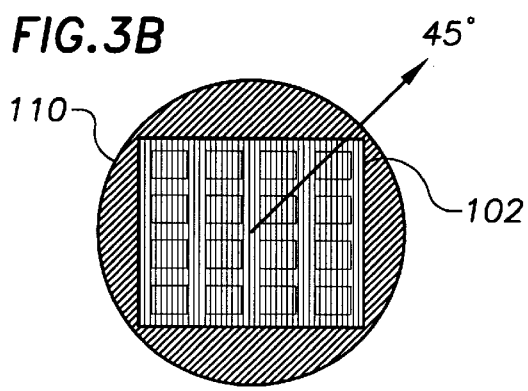
Figure 3D:
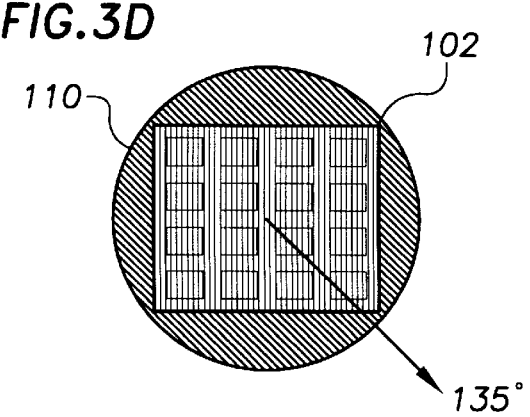
Figure 3C:
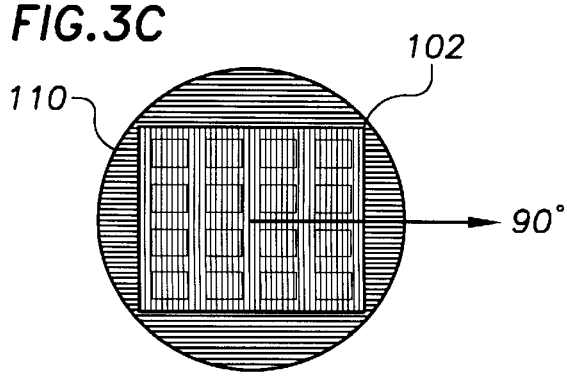

Referring now to FIG. 2, a rear view of an example imaging system 200 is made in accordance with one embodiment of the invention. Common elements of the invention between the figures will use the same numbers, with new numbers being introduced for new elements. System 200 includes sensor 100 that is rotated in front of array 102 via a rotator arrangement 202 that engages a portion of rotatable disk 110. Rotator arrangement 202 imparts a selected rotation rate, or frequency of rotation, on rotatable disk 110 via a gear 204, having gear teeth 206, and a rotating mechanism 208 (e.g., a motor). In another embodiment, disk 110 is rotated via a roller 204A that engages a roller surface 206A with disk edge 111A. Roller 204A could also engage disk 110 via a band that is positioned around disk 110 for imparting a rotation on the disk.

Rotator arrangement 202 is coupled to a detect module 210 that senses the rotation frequency of disk 110 and senses the photocurrent signals generated by array 102. As disk 110 rotates, module 210 generates a set of polarization vector data from the photocurrent signals generated by array 102. Photocurrent signals are sampled as a function of the angular position of disk 110 with respect to the frequency of rotation. The polarization vector data is then converted The present invention facilitates the construction of mechanically rotating filters that are compact and that do not generate high levels of vibration during operation. The present invention is believed to be applicable to a variety of applications involving imaging systems and target acquisition systems. Other aspects and embodiments of the present invention beyond those specifically described herein will be apparent to those skilled in the art from consideration of the specification and practice of the invention disclosed herein. It is intended that the specification and illustrated embodiments be considered as examples only, with a true scope and spirit of the invention being indicated by the following claims.

What is claimed is:

1. An imaging sensor for polarizing light from a light source comprising:
    an array of light detecting elements that converts light from the light source into a plurality of photocurrent signals;
    a rotatable disk positioned between the light source and the light detecting array, the disk being parallel to the light detecting array and including a plurality of linear members that polarize light from the light source passed to the light detecting array, the linear members being opaque and parallel to each other;
    a circuit arrangement configured to generate a data set of polarization vector components and generate a set of Stokes vectors from sampling the polarization vector components, the polarization vector components being generated as a function of a set of the photocurrent signals that are sampled as a function of a position of the rotating disk; and
    a data processing arrangement coupled to the circuit arrangement, the data processing arrangement config-
ured to identify an object as a function of an intensity of the detected light reflected from the object and the vector component data set.

2. The sensor of claim 1, wherein the circuit arrangement in combination with the data processing arrangement are configured to sample the photocurrent signals multiple times during a full rotation of the disk.

3. The sensor of claim 2, wherein the photodetector array is in a substantially fixed position and is spaced at a predetermined distance from the rotatable disk to avoid optical attenuation.

4. The sensor of claim 1, wherein grating formed by the opaque linear members include a series of fused silica lines formed on an optically translucent substrate.

5. The sensor of claim 1, wherein the plurality of opaque linear members includes a set of wire members.

6. The sensor of claim 1, wherein a depth and a width of the plurality of opaque members is a function of the wavelength of the light being detected by the light detecting array.

7. A polarimetric infrared imaging sensor arrangement for generating polarization vector data from light reflected from an object, the vector data for use in object identifcation, the sensor arrangement comprising:
    a photodetector that includes an array of infrared radiation detectors and having an optically transparent surface and arranged to convert detected light reflected from the object into a plurality of photocurrent signals;
    a rotatable disk positioned between the object and the photodetector array and parallel to the photodetector array, the rotatable disk including a plurality of linear members that are opaque and parallel to each other, whereby the reflected light is polarized and passed to the photodetector array;
    a rotator arrangement engaged with a portion of the rotatable disk, the rotator arrangement arranged to impart a selected rotation rate to the rotatable disk; and
    a circuit arrangement coupled to the photodetector array and configured to generate a set of polarization vector data by sampling the photocurrent signals.

8. The sensor arrangement of claim 7, wherein the circuit arrangement is further configured to generate a set of Stokes vectors from sampling the polarization vector components.

9. The sensor arrangement of claim 8, further comprising a data processing arrangement coupled to the circuit arrangement that is adapted to classify the object as a function of an intensity of the detected light originating from the object and the set of Stokes vectors.

10. The sensor arrangement of claim 9, wherein the rotator arrangement includes a gear and motor arrangement that engages a plurality of gears disposed on a circumference edge of the rotatable disk for rotating the rotatable disk.

11. The sensor arrangement of claim 9, wherein the rotator arrangement includes a roller and motor arrangement that engages a circumference edge of the rotatable disk for rotating the rotatable disk.

12. The sensor arrangement of claim 8, wherein the photocurrent signals are sampled when the rotatable disk is at 0, 45, 90 and 135 degrees from a selected starting point.

13. The sensor arrangement of claim 7, wherein the opaque linear members include a set of wire members.

14. The sensor arrangement of claim 7, wherein the opaque linear members include a series of etched lines on an optically transparent disk.

15. A method of identifying an object using light reflected from the object in a target classification system, the method comprising the steps of:
    converting light detected from the object into a plurality of photocurrent signals using a photodetector array;

rotating disk positioned in front of and parallel to the photodetector array, the disk including a plurality of opaque linear members that filter light before being detected by the photodetector array;

sampling the plurality of photocurrent signals at the photodetector array at selected disk angles as the disk rotates;

generating a data set of polarization vector components from the sampled plurality of photocurrent signals; and classifying the object as a function of an intensity of the detected light originating from the object and a set of Stokes vectors generated from the polarization vector components.

16. A system for identifying an object using light reflected from the object in a target classification system, the system comprising:

a photodetector array that converts light detected from the object into a plurality of photocurrent signals;

means for rotating a disk positioned in front of and parallel to the photodetector array, the disk including a plurality of opaque linear members that filter light before being detected by the photodetector array;

means for sampling the plurality of photocurrent signals at the photodetector array at selected disk angles as the disk rotates;

means for generating a data set of polarization vector components from the sampled plurality of photocurrent signals;

means for classifying the object as a function of an intensity of the detected light originating from the object and a set of Stokes vectors generated from the polarization vector components.

* * * * *